United States Patent [19]
Harrod et al.

[11] Patent Number: 6,018,067
[45] Date of Patent: Jan. 25, 2000

[54] PROCESS OF PURIFYING DIHYDROCARBYLCHLOROTHIOPHOSPHATES

[75] Inventors: William B. Harrod, Baton Rouge; David Edward Raposa, Minden, both of La.; Dean Allen Raucstadt, Magnolia, Ark.; Donald S. Vash, Baton Rouge, La.

[73] Assignee: Albemarle Corporation, Richmond, Va.

[21] Appl. No.: 09/249,361

[22] Filed: Feb. 12, 1999

[51] Int. Cl.$^7$ ........................................... C07F 9/14
[52] U.S. Cl. ............................. 558/148; 558/202
[58] Field of Search ............................................... 558/148

[56] References Cited

U.S. PATENT DOCUMENTS

| | | | |
|---|---|---|---|
| 3,089,890 | 5/1963 | Chupp et al. | 260/461 |
| 4,247,490 | 1/1981 | Bergeron et al. | 558/148 |

*Primary Examiner*—Michael G. Ambrose
*Attorney, Agent, or Firm*—Philip M. Pippenger

[57] ABSTRACT

Crude dihydrocarbylchlorothiophosphate product contaminated with dihydrocarbylpolysulfide and/or dihydrocarbylchlorophosphate is upgraded by treating the crude product with an aqueous hypochlorite solution, and separating an aqueous phase from the organic, then drying to obtain the resultant product.

21 Claims, No Drawings

PROCESS OF PURIFYING DIHYDROCARBYLCHLOROTHIOPHOSPHATES

BACKGROUND

As noted in U.S. Pat. No. 3,089,890 to Chapp and Newallis, dihydrocarbylchlorothiophosphates (a.k.a. O,O-dihydrocarbylphosphorochloridothioates), such as diethylchlorothiophosphate are of considerable value as intermediates in the manufacture of pesticidal agents, and can also be used for manufacture of other types useful products.

In the production of dihydrocarbylchlorothiophosphates, small amounts of an undesirable dihydrocarbylpolysulfide coproduct, typically a dihydrocarbyltrisulfide, tend to be formed. Even amounts of less than 0.5 wt % in the dihydrocarbylchlorothiophosphate reaction product is of concern because of its highly disagreeable, persistent odor. Usually still another undesirable coproduct is formed during the production of the dihydrocarbylchlorothiophosphate. This impurity is the oxygen analog of the desired product, i.e., the corresponding dihydrocarbylchlorophosphate, the separation of which is addressed in the foregoing Chapp and Newallis patent. Unfortunately, although this latter impurity can be effectively removed to satisfactorily low levels by the aqueous washing and extraction procedure described in that patent, the Chapp and Newallis procedure described in the patent is incapable of removing the offensive dihydrocarbyltrisulfide impurity to the low levels desired in the final product.

A need thus exists for an effective, commercially feasible way of upgrading the quality of dihydrocarbylchlorothiophosphates by removing therefrom the dihydrocarbylpolysulfide impurities, notably the dihydrocarbyltrisulfide, if not completely, then at least to acceptably low levels. At the same time it would be highly advantageous if the procedure would have the capability of concurrently removing the dihydrocarbylchlorophosphate impurity, when copresent, to satisfactorily low levels. It would also be desirable to provide a new, efficient way of removing dihydrocarbylchlorophosphate from crude dihydrocarbylchlorothiophosphates, or at least reducing the dihydrocarbylchlorophosphate impurity content of crude dihydrocarbylchlorothiophosphates, in any situation where no dihydrocarbylpolysulfide impurity is copresent.

BRIEF SUMMARY OF THE INVENTION

Process technology has now been discovered which is capable of fulfilling the foregoing needs in a highly efficient manner. This is accomplished by use of aqueous hypochlorite as a treating agent.

Accordingly, this invention provides a process of upgrading a crude dihydrocarbylchlorothiophosphate product contaminated with at least one dihydrocarbylpolysulfide and/or at least one dihydrocarbylchlorophosphate, which process comprises contacting the crude product with an aqueous hypochlorite solution, and separating an aqueous phase from the resultant product. By mixing the aqueous hypochlorite solution with the crude dihydrocarbylchlorothiophosphate, the quality of the crude product is improved—i.e., the impurity content of the crude product is reduced. And since the treated dihydrocarbylchlorothiophosphate has relatively poor solubility in water, the process results in the formation of an organic (purified product) phase and an aqueous phase containing the water-soluble products formed by the interaction of the hypochlorite with the impurities. This in turn facilitates the separation, as the phases can be readily separated from each other by decantation.

The mixing of the aqueous hypochlorite with the crude dihydrocarbylchlorothiophosphate results in chemical interaction with at least the dihydrocarbylpolysulfide impurity or impurities. The nature and mechanism(s) involved in such interaction is not known with any degree of certainty. It appears however that in situ generation of chlorine may play a role in the purification reactions. It is also possible that oxidative interaction may be involved at least to some extent. Whatever the mechanism(s) may be, the purification reaction or reactions involved in removing the polysulfide impurity is/are rapid, and the purification reaction or reactions involved in removing the phosphate impurity although less rapid, do not necessitate long residence times in the hypochlorite treatment step.

Preferably, the initial crude product subjected to the process of this invention is a distilled crude product. However this is not a requirement as benefits can be realized by conducting the process with non-distilled reaction product mixtures.

Another feature of this invention is that the purification process can be, and preferably is, conducted as a continuous process, although it can be performed as a batch process or as a semi-continuous process, if desired.

If desired, one or more aqueous extractions of the product can be conducted before and/or after the separation of the aqueous phase resulting from the hypochlorite treatment.

The above and other embodiments of this invention will be still further apparent from the ensuing description and appended claims.

FURTHER DETAILED DESCRIPTION

Dihydrocarbylchlorothiophosphates which can be purified pursuant to this invention are adequately described in U.S. Pat. No. 3,089,890, supra. Thus the hydrocarbyl groups are free of non-benzenoid unsaturation, and typically each such group (e.g., alkyl, cycloalkyl, cycloalkylalkyl, aryl, alkylaryl, aralkyl, etc.) contains 1 to about 8 carbon atoms. A few examples of such compounds include dimethylchlorothiophosphate, dipropylchlorothiophosphate, diisopropylchlorothiophosphate, dibutylchlorothiophosphate, diisobutylchlorothiophosphate, dipentylchlorothiophosphate, dihexylchlorothiophosphate, dioctylchlorothiophosphate, dicyclopentylchlorothiophosphate, dicyclohexylchlorothiophosphate, di(cyclopropylcarbinyl)chlorothiophosphate, diphenylchlorothiophosphate, ditolylchlorothiophosphate, dibenzylchlorothiophosphate, and their analogs and homologs containing up to about 8 carbon atoms in each hydrocarbyl group. Because of its present substantial industrial importance, the process of this invention is preferably applied to the purification of diethylchlorothiophosphate. The only requirement is that the crude dihydrocarbylchlorothiophosphate subjected to the process contains (i) at least one dihydrocarbylpolysulfide impurity or (ii) at least one dihydrocarbylchlorophosphate impurity, or (iii) a combination of (i) and (ii). The process of this invention is preferably, applied to crude dihydrocarbylchlorothiophosphates that are contaminated with at least one dihydrocarbylpolysulfide impurity or with the combination of at least one dihydrocarbylpolysulfide impurity and at least one dihydrocarbylchlorophosphate impurity. Small amounts of other conventional impurities should not have any material adverse effect upon the efficacy of the purification process of this invention, but should be removed if perchance they do exert such an effect.

The process of this invention thus can be applied to crude dihydrocarbylchlorothiophosphate product produced by any process that results in the presence in the product (preferably a distilled product) of at least one dihydrocarbylpolysulfide impurity and/or at least one dihydrocarbylchlorophosphate impurity. The amount of such impurity or impurities in the crude dihydrocarbylchlorothiophosphate product is not critical as the purification process of this invention has the capability of removing any quantity typically found in the product. Typically the amounts of either or both of these two types of impurities (i.e., dihydrocarbylpolysulfide and dihydrocarbylchlorophosphate) will not exceed about 2 wt % of the weight of the pure dihydrocarbylchlorothiophosphate, and in most cases will be much lower than 2 wt %.

The mechanism by which the dihydrocarbylpolysulfide impurity is formed is not known. However, without being bound by theory, a possible explanation of the formation of such impurity may involve in whole or in part a reaction such as:

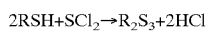

$$2RSH+SCl_2 \rightarrow R_2S_3+2HCl$$

At least in the case of diethylchlorothiophosphate production, the presence of ethyl mercaptan (EtSH) in distillation columns has been observed, presumably as a product of decomposition of nonvolatile organic thiophosphates located in the reactor.

Any water-soluble inorganic hypochlorite, e.g., sodium or potassium hypochlorite, can be used in solution or produced for use in forming the treating agent solution. Preferably, the hypochlorite solution is a buffered aqueous solution. As buffering agents, alkali or alkaline earth hydroxides such as sodium hydroxide, potassium hydroxide, calcium hydroxide or barium hydroxide; alkali or alkaline earth bicarbonates such as sodium bicarbonate or potassium bicarbonate; or other similar water-soluble alkaline media (e.g., lime) can be employed. Typically the solution is buffered to a pH in the range of about 4 to about 12. A commercially-available solution marketed under the trade designation "Chlorox" is convenient solution for use as a treating agent pursuant to this invention. Typically, the treating solution will contain a minimum of about 5% of available chlorine as hypochlorite.

The amount of hypochlorite treating solution used will of course be dependent upon the impurity content of the particular dihydrocarbylchlorothiophosphate product being treated. Normally an excess of hypochlorite solution relative to the impurity content is mixed with the crude product, the excess being an amount sufficient to reduce content of the dihydrocarbylpolysulfide and/or dihydrocarbylchlorophosphate present to at least an acceptable level. For example, in the case of diethylchlorothiophosphate it is, possible to reduce the content of diethyltrisulfide to 0.05% or less, which percentage is a GC area percentage as determined with use of a thermal conductivity detector. At the same time, levels of diethylchlorophosphate of 0.05% or less as determined by GC have been achieved.

In cases where the impurity to be removed in whole or in part is one or more dihydrocarbylpolysulfides such as a dihydrocarbyltrisulfide, and the crude dihydrocarbylchlorothiophosphate contains either no dihydrocarbylchlorophosphate or an amount thereof that is sufficiently low as to require little if any removal from the crude product, the contact time between the hypochlorite solution and the crude in well-agitated mixtures can be very short, e.g., in the range of about 0.5 to about 1.0 minute. However in cases where the content of dihydrocarbylchlorophosphate impurity is to be significantly reduced, a longer contact time should be used, e.g., in the range of about 4 to about 10 minutes. It will be appreciated that even longer times than specified in the foregoing ranges can be used pursuant to this invention whenever deemed necessary or desirable under the particular circumstances involved. With impurity levels typically found in distilled crude diethylchlorothiophosphate, the purification reactions are often completed in 10 minutes or less.

The hypochlorite treating reaction(s) tend to be exothermic and thus it is possible to perform the hypochlorite treatment step involving the contacting and/or mixing of the treating solution and crude product with agitation and without addition of additional thermal energy. However the reactions in the treated mixture can be conducted at temperatures below or above an exothermically-produced temperature, either by cooling or heating the mixture and/or by precooling or preheating the crude product with which the treating solution is being mixed. In general, the hypochlorite treatment step can be performed at temperatures above about 25–30° C. and below the thermal decomposition temperature of the dihydrocarbylchlorothiophosphate being treated. With temperatures above about 100° C., the operation is conducted at superatmospheric pressure to maintain the reactor contents in the liquid state. Preferably, the temperature or temperatures of the mixture during the hypochlorite treatment is/are in the range of about 65 to about 70° C.

It is to be understood and appreciated that although it appears that the hypochlorite treatment may involve some in situ generation or liberation of chlorine, the mechanisms by which the purification reaction or reactions take place is unknown. One possible mechanism that may occur is that chlorine liberated from the hypochlorite may in turn interact with one or more impurity components present in the crude product to form one or more intermediates which in turn interact with the unreacted impurity or impurities, such as a dihydrocarbylpolysulfide. For example, it is conceivable that the liberated chlorine may immediately react in whole or in part with a dihydrocarbyl polysulfide, impurity such as diethyltrisulfide to form an intermediate species which in turn may further react with remaining impurity content. On the other hand, reaction between liberated chlorine and the dihydrocarbylpolysulfide might itself be directly responsible for the destruction of the polysulfide. For instance, it is possible that upon reaction of chlorine with diethyltrisulfide at low levels, sulfur of the polysulfide may be chlorinated selectively, with low levels of chloroethane being evolved upon excess halogenation, perhaps in accordance with the equation:

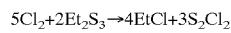

$$5Cl_2+2Et_2S_3 \rightarrow 4EtCl+3S_2Cl_2$$

It is also possible that one or more oxidation reactions occur that contribute to the purification. But whatever the actual mechanism(s) of the hypochlorite treatment, it works—the levels of dihydrocarbyl polysulfide and dihydrocarbylchlorophosphate impurities in the dihydrocarbylchlorothiophosphate can be reduced by the process. Thus this invention is not to be limited by any theory or mechanism of reaction. All that is necessary is to contact the crude dihydrocarbylchlorothiophosphate with the aqueous hypochlorite solution under the appropriate conditions described herein, and ensure that the water-soluble impurities formed in the process are removed from the so-treated dihydrocarbylchlorothiophosphate in an aqueous phase.

In a preferred embodiment, the product after treatment with the hypochlorite is treated or washed with an aqueous solution of a base such as aqueous $Na_2SO_3$, $K_2SO_3$, $NaHSO_3$, $KHSO_3$, NaOH, KOH, or the like, to neutralize acidic materials that may be produced in the hypochlorite reaction(s) such as sulfur monochloride, and to extract the water-soluble products formed by such reaction(s). This operation is typically conducted at one or more temperatures in the range of about 65 to about 75° C. For maximum efficiency the mixture of aqueous and organic phases should be well agitated to ensure intimate contact between the phases. Thereafter the product can be washed with water. Separation(s) of the aqueous and organic (product) phases yields the purified dihydrocarbylchlorothiophosphate.

As an illustration, one such operation can involve an aqueous NaOCl bleach treatment of diethylchlorothiophosphate with a residence time of 1 minute at 58° C. A yield loss of up to 4% (on the test product) can accompany this step, depending on mixing and bleach utilization. In this step the diethyltrisulfide impurity is removed and the residues therefrom are carried away with the aqueous phase. A second step, a caustic wash at 60° C. for 10 minutes, can then be carried out in order to remove other water-soluble impurities such as residual diethylchlorophosphate and nonvolatile organic phosphate dimers and trimers.

As indicated above, the hypochlorite purification treatment process can be conducted as a continuous process. In one preferred form of such process a crude dihydrocarbylchlorothiophosphate product contaminated with at least one dihydrocarbylpolysulfide and/or at least one dihydrocarbylchlorophosphate is continuously introduced into a reaction vessel while concurrently introducing into the vessel (either intermittently with short intervals of time between introductions or, preferably, continuously) an aqueous solution (preferably a buffered alkaline aqueous solution) of a water-soluble hypochlorite, while agitating the contents of the reaction vessel to ensure intimate contact between the feeds, and concurrently withdrawing contents from the reaction vessel at a volumetric rate substantially equivalent to the volumetric rate at which the feeds are being introduced. If the process is basically a single stage purification process, the contents withdrawn from the reaction vessel are then subjected to a phase separation whereby the aqueous phase is separated from the resultant treated product, preferably continuously. When the process is basically a two-stage purification process, the contents withdrawn from the reaction vessel are then continuously fed into a vessel and mixed therein with an aqueous solution of a base such as NaOH, KOH, $Na_2CO_3$, lime, or other alkaline reaction media in order to further reduce the content of dihydrocarbylchlorophosphate impurity. The aqueous base can be continuously or incrementally introduced into such vessel. The contents of the vessel are preferably withdrawn therefrom at a rate comparable to rates of the incoming flows. Also the system should be designed to provide for a residence time of the agitated two-phase mixture sufficient to effect the desired further reduction in phosphate impurity content. Typically residence times for the treatment with aqueous base solution within the range of about 7 and about 10 minutes are sufficient. However longer periods may be used whenever deemed necessary or desirable.

The following Examples illustrate the practice of the process of this invention. These Examples are not intended, however, to limit the scope of the invention. The analyses in the Examples were carried out using a capillary gas chromatographic procedure for the determination of diethylchlorothiophosphate (DECTP) and its minor impurities. In this procedure, DECTP (2 uL) is injected without solvent dilution into a Hewlett-Packard Model 5890 gas chromatograph equipped with a temperature programmer, a 25 m×0.32 mm I.D. fused silica capillary column (Quadrex 5 $\mu$, crosslinked SE-54), and a low volume thermal conductivity detector. The injector temperature was held at 150° C. and the detector was kept at 275° C. Helium carrier gas was used at a flow rate of 5 mL/min through the column with a splitter vent flow rate of 100 mL/min. The oven was temperature programmed linearly: 100° C. initially, held 4 minutes and increased at a rate of 15° C./minute to 160° C. The retention times of DECTP, DECP, and $Et_2S_3$ were 10.1, 9.0, and 10.7 minutes, respectively. The peaks of all components were integrated with a digital integrator and calculated as normalized area percentages.

EXAMPLE 1

Aqueous sodium hypochlorite bleach (75 mL of 5.25% NaOCl) was added by addition funnel into a stirring 250 mL three necked round bottomed flask containing 75 mL diethylchlorothiophosphate (DECTP). An exotherm from 47° C. to 53° C. was seen at atmospheric pressure. A sample of the organic phase was obtained for analysis before and after 15 minutes of reaction time. A 4 mL aliquot was quenched into 10 mL of 2.5%) aqueous NaOH, the phases were separated, and the organic phase was dried over 5 Å molecular sieves and analyzed by GC using the method as described above. The analyses showed that the starting DECTP contained 98.42% DECTP, 0.15% triethylthiophosphate (TETP), 0.07% $Et_2S_3$, and 0.13% diethylchlorophosphate (DECP). The treated product analysis showed 98.87% DECTP, 0.03% TETP, 0.01% $Et_2S_3$, and 0.02% DECP, along with traces of less volatile impurities.

EXAMPLE 2

The procedure of Example 1 was repeated using the same amounts of the materials and the same reaction conditions. The exotherm observed was 47 to 55° C. and the product obtained from the same feedstock as above gave, after 15 minutes of reaction time, 98.90% DECTP, 0.03% TETP, 0.01% $E_2S_3$, and the less volatile impurities noted above.

EXAMPLE 3

A sample of DECTP was prepared which contained 93.16% DECTP, $C_{14}$ internal standard (300 ppm), 0.26% DECP, and 0.09% $Et_2S_3$. A set of 7 runs was carried out in which the same aqueous NaOCl solution was added to and mixed with separate portions (typically 100 mL) of this DECTP sample in various proportions. The specific details regarding amounts used, temperature, and addition time are summarized in the Table along with the analytical results on the 7 treated DECTP products.

TABLE

Reduction of $Et_2S_3$ Levels in DECTP Using Commercial and Buffered Bleach Solutions

| Run No. | mL of Bleach | Temp. ° C. | Addition time, minutes | $Et_2S_3$, GC% |
|---|---|---|---|---|
| 1 | 40 | 65–67 | 2–3 | 0.02 |
| 2 | 40 | 48 | 3 | <0.01 |
| 3 | 38 | 67 | 3 | 0.02 |
| 4 | 38 | 44–47 | 14 | 0.04 |
| 5 (a) | 38 | 40 | 3 | 0.02 |
| 6 (b) | 38 | 55–60 | 8 | 0.09 |
| 7 (c) | 32 | 48–50 | 3 | 0.00 |

(a) Water, 10 mL, was added for dilution.
(b) Reversed addition: DECTP was added into the bleach solution. A strong exotherm 30–70° C. was observed.

TABLE-continued

Reduction of Et$_2$S$_3$ Levels in DECTP Using
Commercial and Buffered Bleach Solutions

| Run No. | mL of Bleach | Temp. °C. | Addition time, minutes | Et$_2$S$_3$, GC% |
| --- | --- | --- | --- | --- |

(c) 84 mL of DECTP was used. Bleach in this run was prebuffered with 7.9% of solid NaHCO$_3$.

In Run 7 of the Table, 0.05% and 0.06%, of two nonvolatile impurities were produced and these were not sufficiently removed by the treatment procedure used.

Example 4 illustrates the conduct of the process on a continuous basis.

EXAMPLE 4

DECTP and aqueous sodium hypochlorite bleach were co-fed into a 20-gallon stirred reactor. Effluent from the 20-gallon reactor was co-fed with NaOH and water into a 100-gallon stirred reactor and the downstream aqueous phase was kept above a pH of 10 by incremental addition of caustic as needed on the basis of tests of the aqueous phase using pH paper. The conditions for this run are given below.

| | |
| --- | --- |
| Bleach reactor temperature: | 100–150° F. (ca. 38–66° C.) |
| Bleach reactor pressure: | 9–20 psig (ca. 163–239 kPa) |
| DECTP flow rate: | 3,000–4,000 lb/hr (ca. 1361–1814 kg/hr) |
| Aqueous bleach flow rate: | 0.8–2.3 gal/min (ca. 3.0–8.7 L/min) |
| % Diethyltrisulfide in feed: | 0.05–0.14 wt % |
| % Diethyltrisulfide trisulfide in treated product: | 0.00–0.04 wt % |
| 25% Caustic flow rate: | 160–240 lb/hr (ca. 73–109 kg/hr) |
| Dilution water flow rate: | 2.5–7 gals/min (ca. 9.5–26.3 L/min) |

It is to be understood that chemical compounds referred to by chemical name or formula anywhere in the specification or claims hereof, whether referred to in the singular or plural, are identified as they exist prior to coming into contact with another substance referred to by chemical name or chemical type (e.g., a reactant, a solvent, a diluent, or etc.). As a result of such contacting one or more chemical changes or transformations such as solvolysis, ionization, complex formation, chemical reaction or the like, may take place, and such changes or transformations, if the result of conducting, an operation or procedure in accordance with this disclosure, are within the scope and contemplation of this invention. Thus there is no requirement that any chemical compound must remain unchanged when mixed with another ingredient, substance or compound as long as the operation or procedure being used is in accordance with the plain and ordinary meaning of this specification using common sense and ordinary knowledge and skill of a person skilled in the art. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Any patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process of upgrading a crude dihydrocarbylchlorothiophosphate product which is contaminated with at least one dihydrocarbylpolysulfide and/or at least one dihydrocarbylchlorophosphate, which process comprises contacting the crude product with an aqueous hypochlorite solution, and separating an aqueous phase from the resultant product.

2. A process according to claim 1 wherein said crude dihydrocarbylchlorothiophosphate product is a distilled dihydrocarbylchlorothiophosphate product contaminated with at least one dihydrocarbylpolysulfide and/or at least one dihydrocarbylchlorophosphate.

3. A process according to claim 1 wherein said crude dihydrocarbylchlorothiophosphate product is a dialkylchlorothiophosphate product contaminated at least with (i) a dialkyltrisulfide or (ii) a dialkyltrisulfide and a dialkylchlorophosphate, and wherein the alkyl groups of the crude dialkylchlorothiophosphate product and the alkyl groups of (i) or (ii), as the case may be, each contain about 8 carbon atoms or less.

4. A process according to claim 3 wherein said dialkylchlorothiophosphate product is a distilled product.

5. A process according to claim 3 wherein said dialkylchlorothiophosphate product is a diethylchlorothiophosphate product contaminated at least with (i) diethyltrisulfide or (ii) diethyltrisulfide and diethylchlorophosphate.

6. A process according to claim 5 wherein said diethylchlorothiophosphate product is a distilled product.

7. A process of any of claims 1–6 wherein the resultant product is subjected to one or more washings with (i) an aqueous solution of a base or (ii) water, or with separate washings with (i) and with (ii).

8. A process of any of claims 1–6 wherein the process is conducted as a continuous process.

9. A process of any of claims 1–6 wherein the aqueous hypochlorite solution is a buffered solution with a pH in the range of about 4 to about 12.

10. A process of reducing or eliminating the diethyltrisulfide content of a crude diethylchlorothiophosphate product which is contaminated at least with diethyltrisulfide, which process comprises mixing the crude product with an aqueous hypochlorite solution, and separating an aqueous phase from the resultant product.

11. A process according to claim 10 wherein said crude diethylchlorothiophosphate product is a distilled diethylchlorothiophosphate product.

12. A process according to claim 10 wherein the resultant product is subjected to one or more washings with (i) an aqueous solution of a base or (ii) water, or with separate washings with (i) and with (ii).

13. A process according to claim 10 wherein said crude diethylchlorothiophosphate product is a distilled diethylchlorothiophosphate product, and wherein the resultant product is subjected to one or more washings with (i) an aqueous solution of a base or (ii) water, or with separate washings with (i) and with (ii).

14. A process according to claim 10 wherein said crude diethylchlorothiophosphate product is also contaminated with diethylchlorophosphate.

15. A process according to claim 10 wherein said crude diethylchlorothiophosphate product is a distilled diethylchlorothiophosphate product, wherein said distilled crude diethylchlorothiophosphate product is also contaminated with diethylchlorophosphate, and wherein the resultant product is subjected to one or more washings with (i) an aqueous solution of a base or (ii) water, or with separate washings with (i) and with (ii).

16. A process according to claim 10 wherein the aqueous hypochlorite solution is a buffered solution with a pH in the range of about 8 to about 12.

17. A process according to claim 10 wherein the process is conducted as a continuous process.

18. A process according to claim 13 wherein the process is conducted as a continuous process.

19. A process according to claim 15 wherein the process is conducted as a continuous process.

20. A process which comprises:
   a) continuously feeding crude dihydrocarbylchlorothiophosphate product contaminated at least with at least one dihydrocarbylpolysulfide and at least one dihydrocarbylchlorophosphate into a reaction zone, and concurrently feeding aqueous hypochlorite solution into the reaction zone, intermittently or continuously, while agitating the mixture in the reaction zone to ensure intimate contact between the feed materials;
   b) continuously feeding a portion of the treated product from the reaction zone to a quenching zone, and concurrently feeding an aqueous alkaline solution into the quenching zone, intermittently or continuously, and agitating the contents of the quenching zone to ensure intimate contact between the resultant aqueous and organic phases in the quenching zone;
   c) continuously withdrawing contents from the quenching zone; and
   d) separating the aqueous and organic phases from each other;

the volumetric rate of the feeds in a) and the volumetric rate at which contents are withdrawn in c) being substantially equivalent, and the volumetric rate of the feeds in b) and the volumetric rate at which contents are withdrawn in c) being substantially equivalent.

21. A process according to claim 20 wherein said crude dihydrocarbylchlorothiophosphate product is a distilled diethylchlorothiophosphate product contaminated at least with diethyltrisulfide and diethylchlorophosphate.

* * * * *